United States Patent
Yeh (10) Patent No.: US 11,484,666 B2
(45) Date of Patent: Nov. 1, 2022

(54) SAFELY NEEDLE

(71) Applicant: CC Biotechnology Corporation, Tainan (TW)

(72) Inventor: Chin-Min Yeh, Tainan (TW)

(73) Assignee: CC Biotechnology Corporation, Tainan (TW)

( * ) Notice: Subject to any disclaimer, the term of this patent is extended or adjusted under 35 U.S.C. 154(b) by 496 days.

(21) Appl. No.: 16/077,941

(22) PCT Filed: Mar. 2, 2016

(86) PCT No.: PCT/CN2016/075319
§ 371 (c)(1),
(2) Date: Aug. 14, 2018

(87) PCT Pub. No.: WO2017/147817
PCT Pub. Date: Sep. 8, 2017

(65) Prior Publication Data
US 2020/0297940 A1  Sep. 24, 2020

(51) Int. Cl.
*A61M 5/32* (2006.01)
*A61M 5/50* (2006.01)
*A61M 5/20* (2006.01)

(52) U.S. Cl.
CPC ........ *A61M 5/3271* (2013.01); *A61M 5/2033* (2013.01); *A61M 5/321* (2013.01);
(Continued)

(58) Field of Classification Search
CPC .............. A61M 5/3271; A61M 5/3202; A61M 5/3213; A61M 5/50; A61M 2005/3247;
(Continued)

(56) References Cited

U.S. PATENT DOCUMENTS

| 5,984,899 | A  |   | 11/1999 | D'Alessio et al. |
| 6,203,529 | B1 | * | 3/2001  | Gabriel ............... A61M 5/3202 604/192 |

(Continued)

FOREIGN PATENT DOCUMENTS

| CN | 1531446    |   | 9/2004  |
| CN | 101219252  | B | 12/2012 |

(Continued)

OTHER PUBLICATIONS

European Patent Office, Extended European Search Report of corresponding European Patent Application No. 16892008.0 dated Aug. 6, 2019, (8 pages).

*Primary Examiner* — Nathan R Price
*Assistant Examiner* — Anh Bui
(74) *Attorney, Agent, or Firm* — Bradley J. Thorson; DeWitt LLP (57) ABSTRACT

A safety needle has a needle base, a puncture needle, and a safety cap. The puncture needle is inserted into a front end of a needle connection segment of the needle base. The safety cap is combined with a front end of the needle base. The safety cap has a needle cap and a resilient member mounted in the needle base. The needle cap is mounted around the puncture needle. Guiding blocks formed on the rear end of the needle cap are mounted respectively in positioning recesses in a housing of the needle base. The needle cap and an outer cap are mounted around the puncture needle, and the puncture needle can be kept from exposure. The needle cap can be locked with the positioning recesses, and the safety needle cannot be reused and can be distinguished as a used needle.

12 Claims, 13 Drawing Sheets

(52) U.S. Cl.
CPC ........ *A61M 5/3202* (2013.01); *A61M 5/3204* (2013.01); *A61M 5/326* (2013.01); *A61M 5/3213* (2013.01); *A61M 5/50* (2013.01); *A61M 5/5086* (2013.01); *A61M 2005/3206* (2013.01); *A61M 2005/3247* (2013.01); *A61M 2205/273* (2013.01)

(58) Field of Classification Search
CPC .... A61M 2205/273; A61M 2005/3267; A61M 5/3272; A61M 5/32; A61M 5/3243; A61M 2005/3258; A61M 5/2033; A61M 5/326; A61M 5/3204; A61M 2005/3206; A61M 5/321; A61M 5/5086
See application file for complete search history.

(56) References Cited

U.S. PATENT DOCUMENTS

| | | |
|---|---|---|
| 2002/0004648 A1 | 1/2002 | Larsen |
| 2005/0113750 A1 | 5/2005 | Targell |
| 2005/0133750 A1 | 6/2005 | Hakamata |
| 2005/0187522 A1 | 8/2005 | Miller |
| 2006/0189933 A1 | 8/2006 | Alheidt et al. |
| 2008/0097310 A1* | 4/2008 | Buehler .................. A61M 5/50 604/111 |
| 2009/0299295 A1* | 12/2009 | Rubinstein ............ A61M 5/326 604/198 |
| 2013/0172818 A1* | 7/2013 | Schraga ........... A61B 5/150648 604/110 |

FOREIGN PATENT DOCUMENTS

| | | |
|---|---|---|
| CN | 104619366 A | 5/2015 |
| CN | 204395141 U | 6/2015 |
| TW | 320564 A | 11/1997 |
| TW | 592742 | 6/2004 |
| TW | 595482 | 6/2004 |
| TW | M504606 U | 7/2015 |
| TW | M513032 U | 12/2015 |
| WO | 200191837 A1 | 12/2001 |
| WO | 0209797 A1 | 2/2002 |
| WO | 2011076280 A1 | 6/2011 |
| WO | WO-2012000834 A1 * | 1/2012 .......... A61M 5/3271 |

* cited by examiner

SAFELY NEEDLE

CROSS-REFERENCE TO RELATED APPLICATIONS

This patent application is a national stage application under 35 U.S.C. 371 and claims the benefit of International Application No. PCT/CN2016/075319, filed on Mar. 2, 2016. The entire contents of which are hereby incorporated herein by reference thereto.

BACKGROUND OF THE INVENTION

1. Field of the Invention

The present invention relates to a safety needle, and more particularly to a safety needle connected with a barrel and applied for injection.

2. Description of Related Art

To protect medical staff from needle-stick injuries and infections, a safety needle is used. A conventional safety needle substantially comprises a puncture needle and an outer cap. The outer cap is mounted around the puncture needle. When the safety needle is in use, a connection portion formed on one end of the puncture needle is mounted around a front end of a syringe barrel. Before injection, the outer cap is kept mounted around the puncture needle to keep the needle from being exposed.

However, although the outer cap mounted around the puncture needle can provide a protective effect, the outer cap cannot completely keep the puncture needle from being exposed when the safety needle is transported or in use. In addition, to recognize whether the conventional safety needle has been used or not is difficult from the appearance of the conventional safety needle, so a used safety needle may be inadvertently reused.

To overcome the shortcomings, the present invention tends to provide a safety needle to mitigate or obviate the aforementioned problems.

SUMMARY OF THE INVENTION

The main objective of the invention is to provide a safety needle that can keep a puncture needle from being exposed when the safety needle is transported or in use and can be easily recognized as a used or unused needle.

The safety needle has a needle base, a puncture needle, and a safety cap. The needle base has a needle connection segment, a barrel connection segment, and a housing. The needle connection segment has a needle hole. The barrel connection segment is formed on a rear end of the needle connection segment. The housing is formed around the needle connection segment to define an annular space between the needle connection segment and the housing and has an opening, an abutting segment, and at least one positioning recess. The opening is defined in a front end of the housing. The abutting segment is formed on a rear end of the housing and is connected with the rear end of the needle connection segment. The at least one positioning recess is formed in an outer surface of the housing, and each one of the at least one positioning recess has a straight section, a guiding section, and a locking section. The straight section extends along a longitudinal direction of the housing. The guiding section is formed in the front end of the housing and has a rear end connected with a front end of the straight section. The locking section is formed in the front end of the housing and has a rear end connected with the front end of the straight section and being in front of the rear end of the guiding section, a locking recess defined in an end of the locking section away from the straight section, and an inclined surface formed on a front end of the locking section and extends from the front end of the straight section toward the locking recess. The guiding section extends toward a direction opposite the inclined surface of the locking section.

The puncture needle is inserted into the needle hole in the needle connection segment, extends out of the front end of the housing of the needle base, and has an axial hole defined axially through the puncture needle and communicating with the needle hole in the needle connection segment.

The safety cap is combined with a front end of the needle base and has a needle cap, a resilient member, and an outer cap. The needle cap has a through hole defined axially through it, at least one guiding block formed on its rear end, and a front end. The resilient member extends into the annular space in the needle base, is mounted around the needle connection segment, and has a front end connected with the rear end of the needle cap and a rear end connected with the abutting segment of the housing. The outer cap is formed integrally and detachably around the needle cap and has a front end and a rear end selectively abutting the front end of the housing of the needle base. The front end of the needle cap is located inside the outer cap. The rear end of the needle cap extends out of the rear end of the outer cap, is held inside the housing, and is mounted around the needle connection segment. A gap is defined between the rear end of the outer cap and the at least one guiding block on the needle cap. The at least one guiding block is held respectively in the at least one positioning recess. The puncture needle is held inside the needle cap and the outer cap.

Wherein, the housing has two positioning recesses diametrically opposite each other; and the needle cap has two guiding blocks diametrically opposite each other and mounted respectively in the positioning recesses.

Wherein, the barrel connection segment of the needle base comprises a sleeve and two screwing blocks formed on a rear end of the sleeve and diametrically opposite each other.

Wherein, the outer cap has multiple connection portions formed on the rear end of the outer cap and formed on an outer surface of the needle cap; and each connection portion has a thickness gradually decreasing toward the needle cap.

Wherein the resilient member is formed integrally on the rear end of the needle cap and comprises one spiral resilient strip or multiple spiral resilient strips.

The present invention can achieve the following advantages.

1. The guiding blocks on the rear end of the needle cap are at an original position which is located at the front end of the guiding section of the at least one positioning recess, and the rear end of the outer cap abuts the front end of the housing of the needle base. Thus, the needle cap is positioned inside the outer cap, and the puncture needle is enclosed inside the needle cap. Accordingly, the puncture needle can be kept from being exposed during the transportation and the operation before an injection process. The safety needle can be easily distinguished as an unused needle.

2. Before the injection process, the outer cap around the needle cap is twisted, and the outer cap is detached from the needle cap. Consequently, the front end of the needle cap of the safety needle connected with the syringe extends toward a patient who is given an injection. During this process, the puncture needle is kept enclosed inside the needle cap to ensure safety of use.

3. After the medication is injected into the patient, the syringe is pulled backward to move the puncture needle out of the patient. At this time, the needle cap is pushed to extend out of the front end of the housing by the resilient member, and the puncture needle is enclosed inside the needle cap. When the needle cap is pushed to move forward by the resilient member, the guiding blocks on the rear end of the needle cap will move from the straight sections of the positioning recesses, will move into the locking sections by the guiding effect provided by the inclined surfaces, and are engaged with the locking recesses. The locked needle cap cannot be pushed into the housing of the needle base, such that the puncture needle can be kept enclosed inside the needle cap. Accordingly, the safety needle cannot be reused and can be easily distinguished as a used needle.

The safety needle in accordance with the present invention may further have multiple connection portions formed on the rear end of the outer cap and formed on an outer surface of the needle cap, and each connection portion has a thickness gradually decreasing toward the needle cap. Accordingly, the outer cap can be twisted to be detached from the needle cap.

The barrel connection segment of the safety needle in accordance with the present invention may further have a sleeve and two screwing blocks formed on a rear end of the sleeve and diametrically opposite each other to connect with a syringe via a screwing collar.

The resilient member of the safety needle in accordance with the present invention may further have one spiral resilient strip or multiple spiral resilient strips and is formed integrally on the rear end of the needle cap. Accordingly, the safety needle can be achieved by the application of the material of high drug-resistance, high biocompatibility, high rigidity or high elasticity, and to assemble the safety needle is convenient.

The safety needle in accordance with the present invention may further have two positioning recesses diametrically opposite each other and two guiding blocks formed on the rear end of the needle cap, diametrically opposite each other and mounted respectively in the positioning recesses. Accordingly, the movement of the needle cap inside the needle base is smooth.

DETAILED DESCRIPTION OF PREFERRED EMBODIMENT

Figure 1:
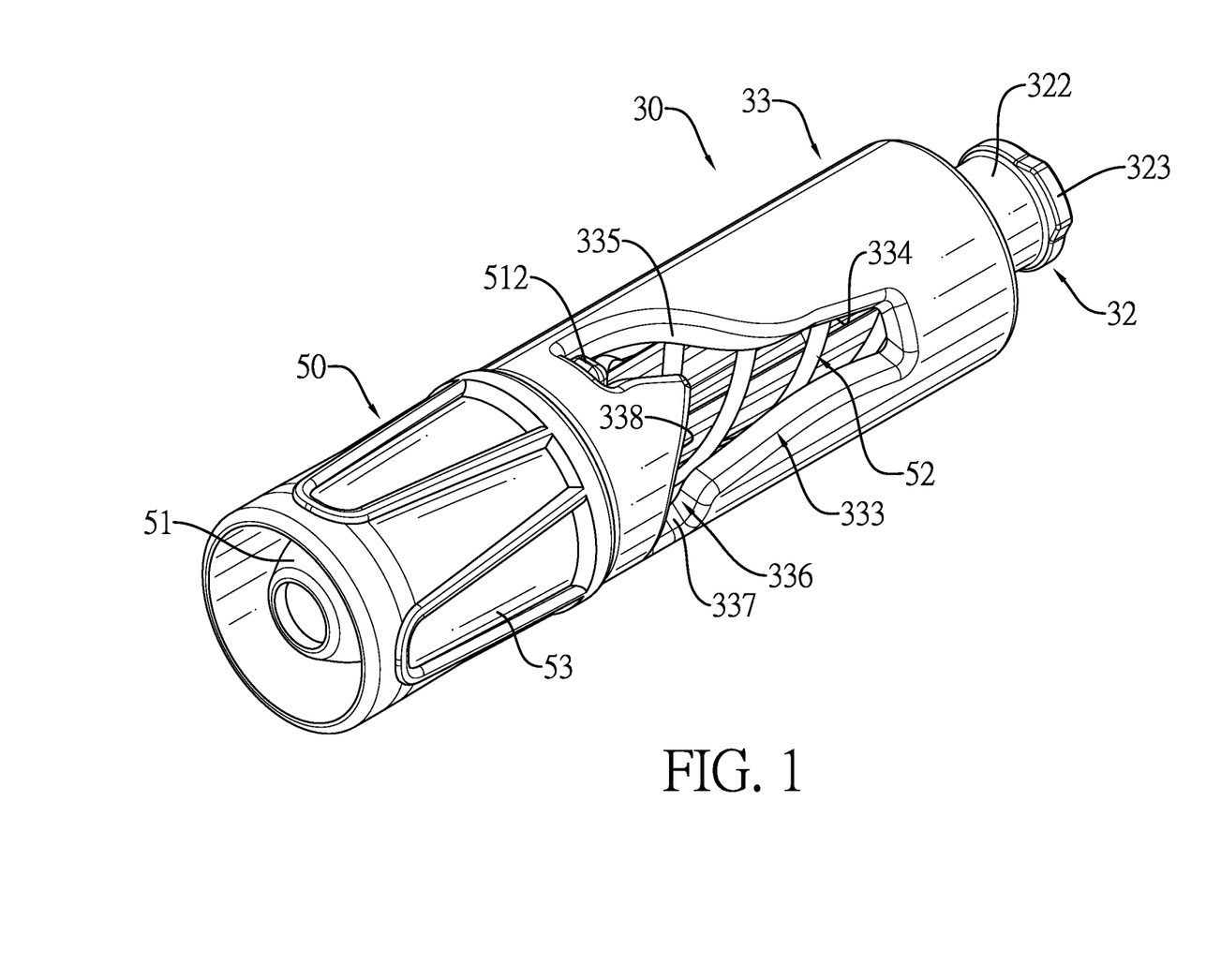
FIG. 1 is a perspective view of a safety needle in accordance with the present invention.
Figure 2:
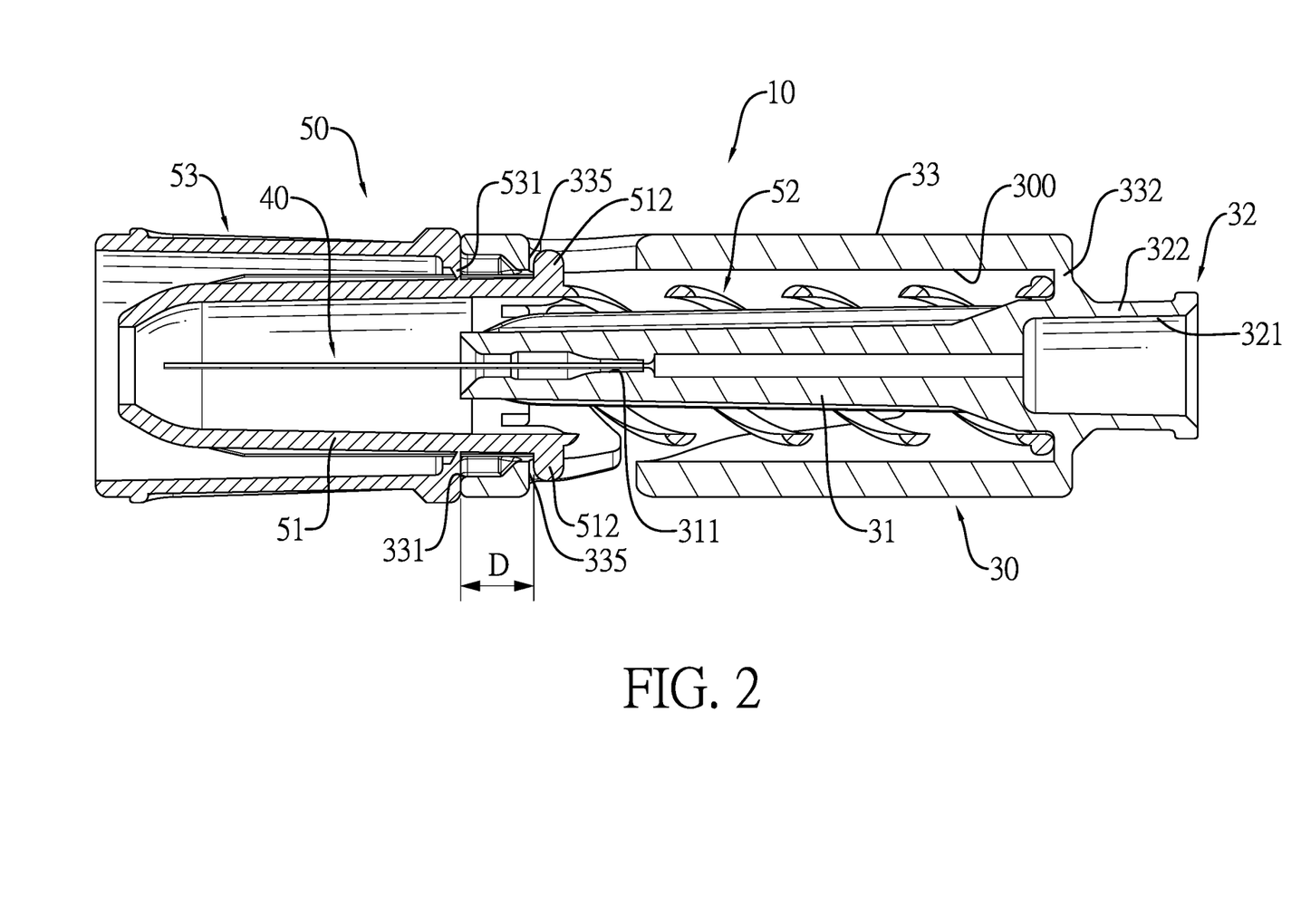
FIG. 2 is a cross sectional side view of the safety needle in FIG. 1.

With reference to FIGS. 1 and 2, a safety needle 10 in accordance with the present invention is adapted to be connected with a front end of a syringe barrel and comprises a needle base 30, a puncture needle 40, and a safety cap 50.

With reference to FIGS. 1 to 4, the needle base 30 comprises a needle connection segment 31, a barrel connection segment 32, and a housing 33. The needle connection segment has a needle hole 311. The barrel connection segment 32 is formed on a rear end of the needle connection segment 31 and has a barrel connection hole 321. The barrel connection hole 321 communicates with a rear end of the needle hole 311 in the needle connection segment 31 and has a diameter larger than a diameter of the needle hole 311. The housing 33 is formed around the needle connection segment 31 to define an annular space 300 between the housing 33 and the needle connection segment 31. An opening 331 is formed in a front end of the housing 33. An abutting segment 332 is formed on a rear end of the housing 33 and is connected with the rear end of the needle connection segment 31.

With reference to FIGS. 1 to 4, at least one positioning recess 333 is defined in an outer surface of the housing 33. In the present embodiment, the housing 33 has two positioning recesses 333 diametrically opposite each other. Each positioning recess 333 comprises a straight section 334, a guiding section 335, and a locking section 336. The straight section 334 substantially extends along a longitudinal direction of the housing 33. The guiding section 335 and the locking section 336 are formed respectively at two sides of a front end of the housing 33. A rear end of the locking section 336 is connected with a front end of the straight section 334 and is in front of a rear end of the guiding section 335 that is also connected with the front end of the straight section 334. The locking section 336 has a locking recess 337 defined in an end of the locking section 336 away from the straight section 334. The locking section 336 has an inclined surface 338 formed on the front end of the locking section 336 and extends from the front end of the straight section 334 toward the locking recess 337. The guiding section 335 extends toward a direction opposite the inclined surface 338 of the locking section 336.

With reference to FIGS. 1 to 4, in the present embodiment, the barrel connection segment 32 connected with the needle connection segment 31 is exposed from a rear end of the abutting segment 332. The barrel connection segment 32 has a sleeve 322 and one or multiple screwing blocks 323 formed on a rear end of the sleeve 322 to connect with a screwing collar and to be locked on a front end of the barrel. The number of the screwing blocks 323 depends on the number of threads of a threaded hole of the screwing collar connected with the barrel connection segment 32. In the present embodiment, the barrel connection segment 32 has two screwing blocks 323 diametrically opposite each other to screw with the screwing collar 23 having two threads.

Figure 3:
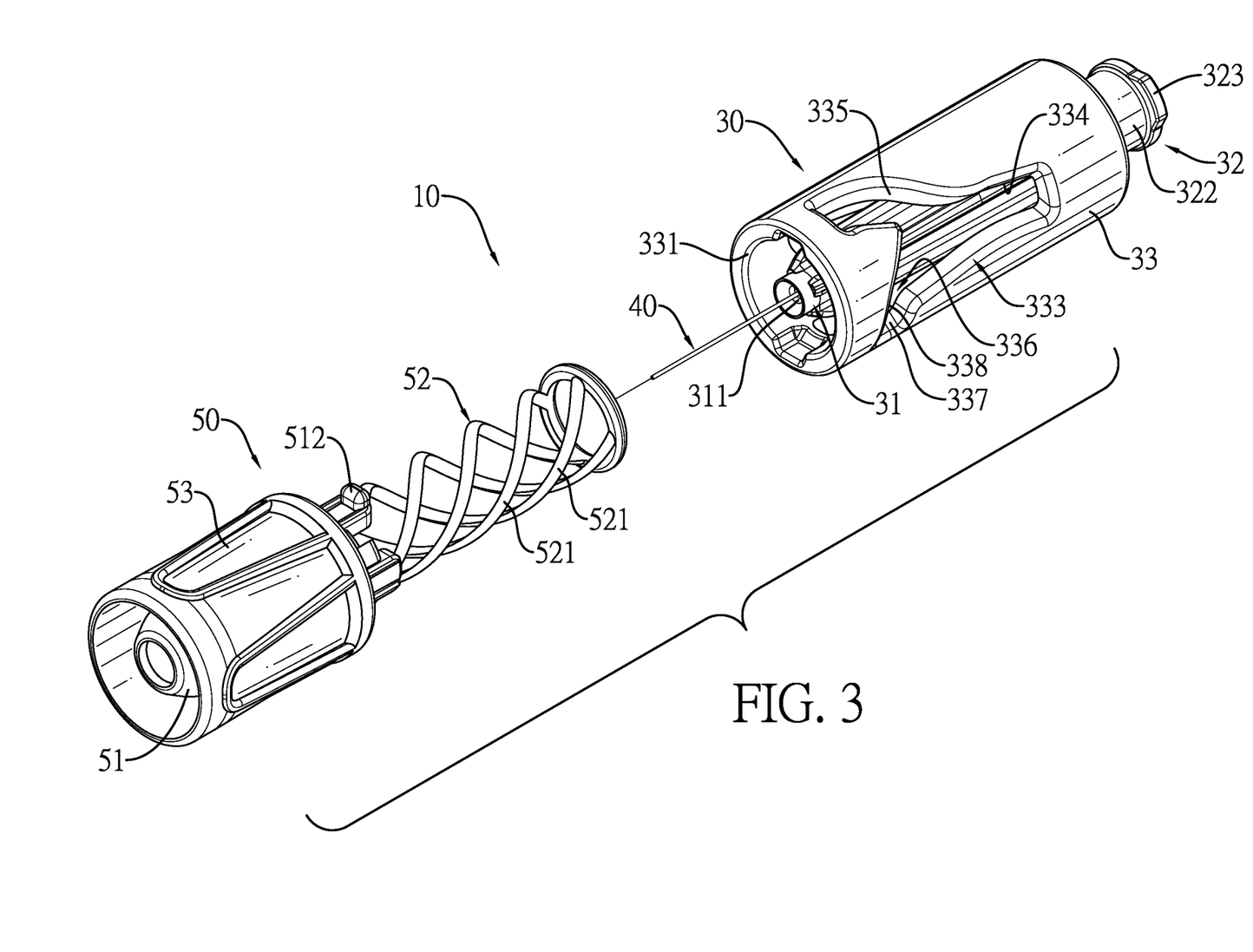
FIG. 3 is an exploded perspective view of the safety needle in FIG. 1.
Figure 4:
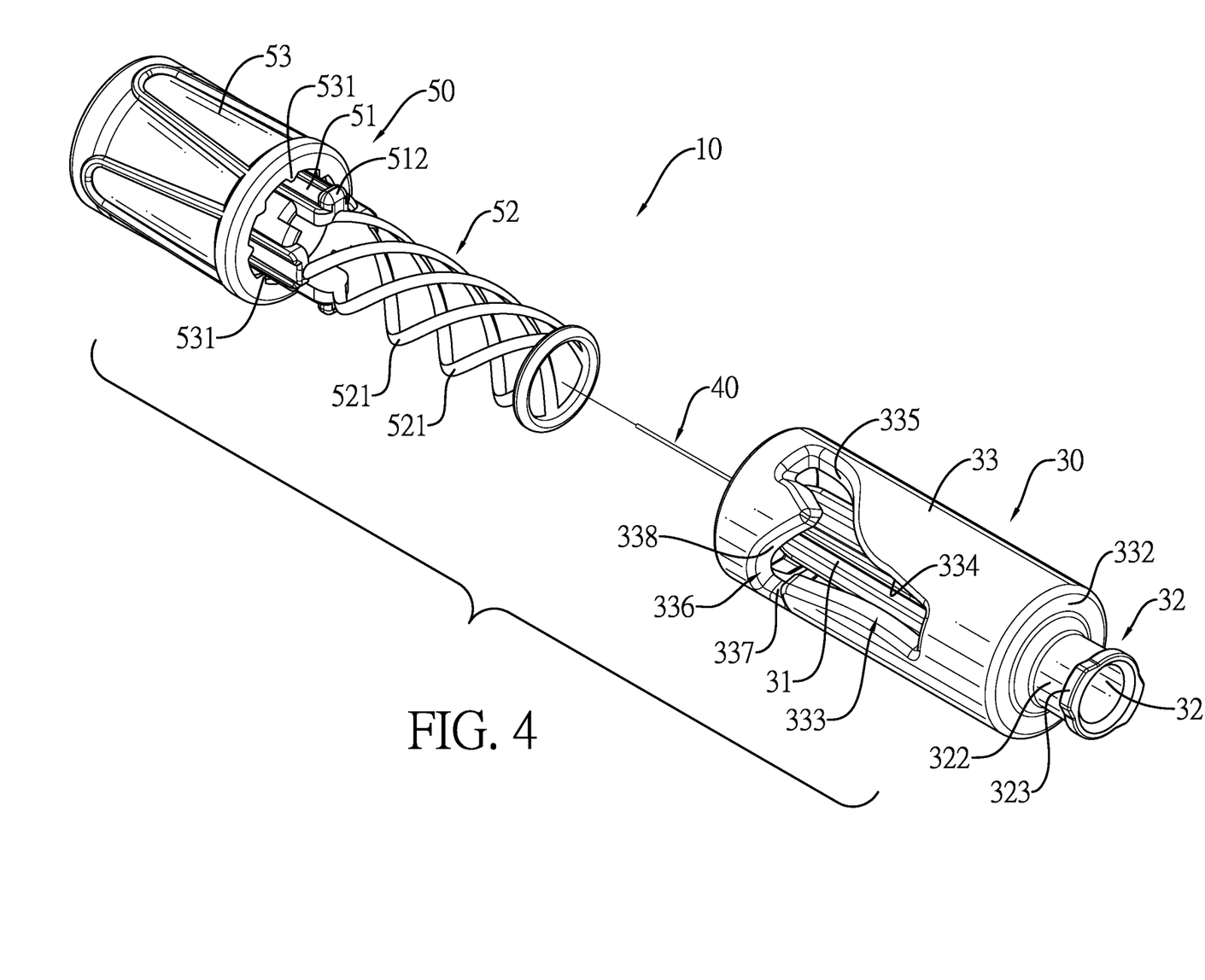
FIG. 4 is another exploded perspective view of the safety needle in FIG. 1.

With reference to FIGS. 2 to 4, the puncture needle 40 has an axial hole defined axially through the puncture needle 40. A rear end of the puncture needle 40 is inserted securely into the needle hole 311 of the needle connection segment 31, and a front end of the puncture needle 40 extends out of the front end of the housing 33 of the needle base 30. The axial hole of the puncture needle 40 communicates with the barrel connection hole 321 in the barrel connection segment 32 via the needle hole 311.

With reference to FIGS. 1 to 4, the safety cap 50 comprises a needle cap 51, a resilient member 52, and an outer cap 53. The needle cap 51 has a through hole axially defined through the needle cap 51. One or multiple guiding blocks 512 are formed on an outer surface of a rear end of the needle cap 51. The resilient member 52 is connected with the rear end of the needle cap 51. The outer cap 53 is mounted around the needle cap 51 and is connected integrally with the needle cap 51 as a single piece. A front end of the needle cap 51 is located inside the outer cap 53. The rear end of the needle cap 51 provided with the guiding blocks 512 extends out of a rear end of the outer cap 53. A gap D is formed between the rear end of the outer cap 53 and the guiding blocks 512 of the needle cap 51.

With reference to FIGS. 1 to 4, the safety cap 50 is combined with the front end of the needle base 30. The resilient member 52 of the safety cap 50 extends into the annular space 300 in the needle base 30 and is mounted around the needle connection segment 31. The rear end of the needle cap 51 provided with the guiding blocks 512 is located inside the housing 33, and the guiding blocks 512 are held in the positioning recesses 333. The rear end of the outer cap 53 is adjacent to or abuts the front end of the housing 33 of the needle base 30. The puncture needle 40 mounted on the front end of the needle base 30 is held inside the outer cap 53 and the needle cap 51. The outer cap 53 can be twisted relative to and detached from the needle cap 51, such that the needle cap 51 can be pushed into the housing 33 of the needle base 30 once the resilient member 52 is compressed, and the puncture needle 40 is exposed. Thus, the needle cap 51 can be pushed out of the housing 33 by the resilient member 52 and can be locked by the locking recess 337 of the locking section 336 of the housing 33. Consequently, the puncture needle 40 is enclosed inside the needle cap 51, and the locked needle cap 51 can be kept from being pushed into the housing 33 of the needle base 30 again.

With reference to FIGS. 1 to 4, the resilient member 52 and the needle cap 51 can be formed as a single piece or are individual components to each other. In the present embodiment, the resilient member 52 is formed integrally on the rear end of the needle cap 51 and comprises one or multiple spiral resilient strips 521. In the present embodiment, the resilient member 52 comprises multiple resilient strips 521. The resilient strips 521 are connected with the rear end of the needle cap 51 and have a compression and recoil resilient force.

Figure 7:
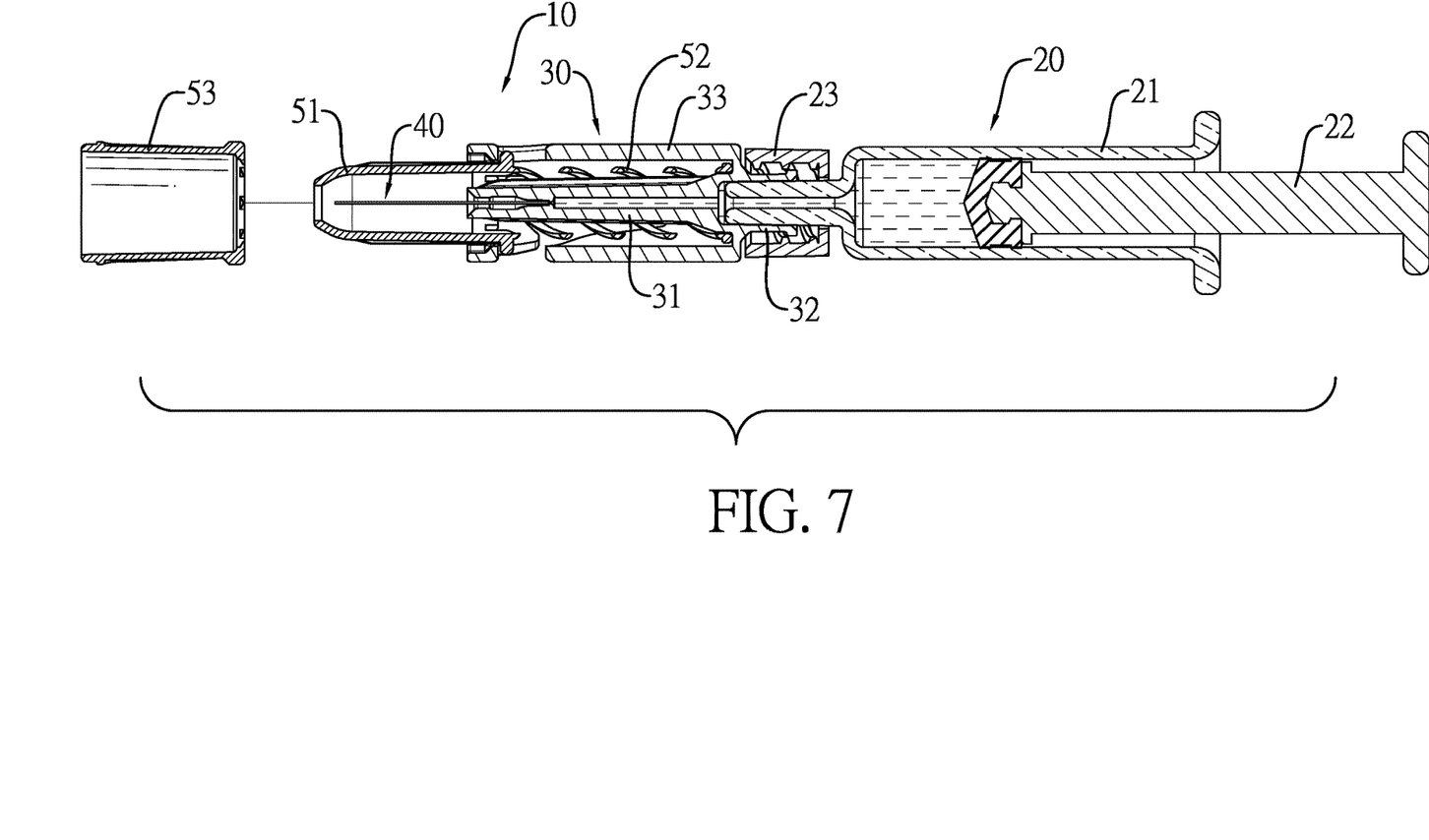
FIG. 7 is an operational cross sectional side view of the safety needle in FIG. 6 connected with a syringe barrel, showing that the outer cap is detached from the needle cap.

With reference to FIGS. 1 to 4, in the present embodiment, the outer cap 53 has multiple connection portions 531 formed on the rear end of the outer cap 53 and formed integrally on an outer surface of the needle cap 51. Each connection portion 531 has a thickness gradually decreasing toward the needle cap 51. With reference to FIGS. 2 and 7, the outer cap 53 can be rotated relative to the needle cap 51, and the conjunctions having a thin thickness between the connection portions 531 and the needle cap 51 will be broken. Thus, the outer cap 53 can be detached from the needle cap 51.

Figure 5:
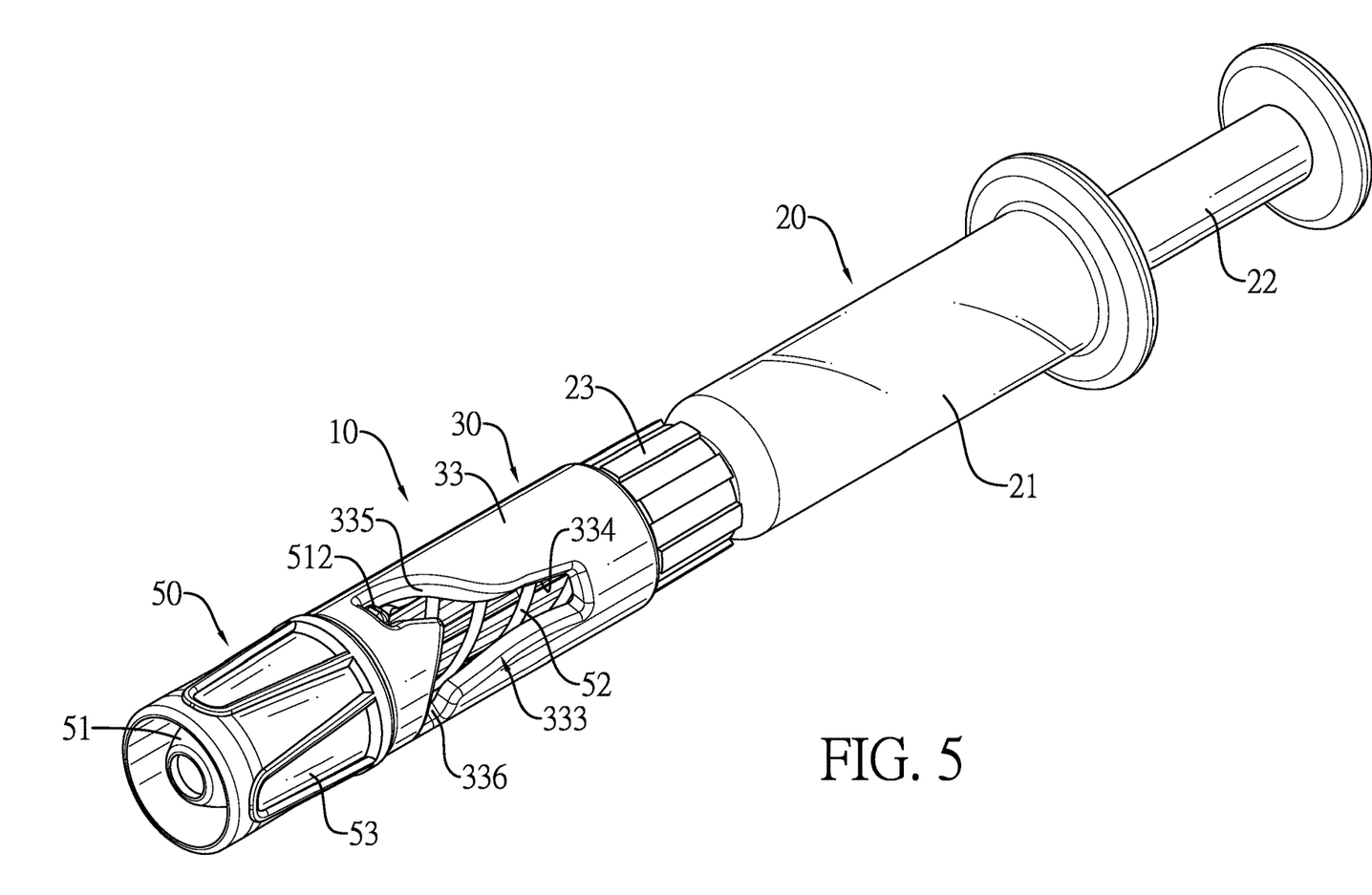
FIG. 5 is a perspective view of the safety needle in FIG. 1 connected with a syringe barrel.
Figure 6:
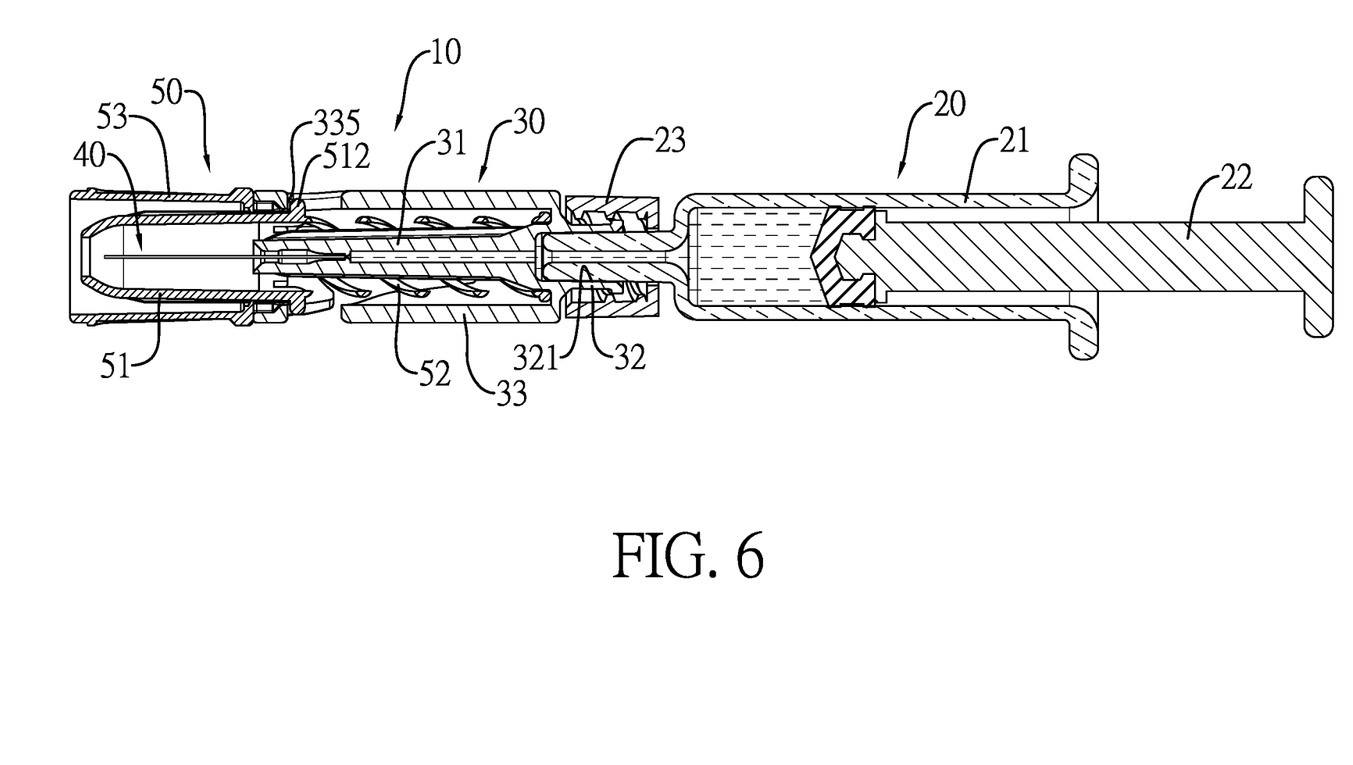
FIG. 6 is a cross sectional side view of the safety needle in FIG. 1 connected with a syringe barrel.

When the safety needle 10 in accordance with the present invention is in use, with reference to FIGS. 5 and 6, the needle base 30 of the safety needle 10 is connected with a screwing collar 23 and is connected securely with a front end of a barrel 21 of a syringe 20 containing medication for injection. The guiding blocks 512 on the needle cap 51 of the safety needle 10 are located at the front ends of the guiding sections 335 of the positioning recesses 333 as an original position. The rear end of the outer cap 53 abuts the front end of the housing 33 of the needle base 30, such that the needle cap 51 is positioned securely inside the outer cap 53 and the puncture needle 40 is enclosed inside the needle cap 51. Accordingly, during the transportation and operation before an injection process, the puncture needle 40 of the safety needle 10 can be completely kept from being exposed, and the safety needle 10 can be easily distinguished as an unused needle.

Figure 8:
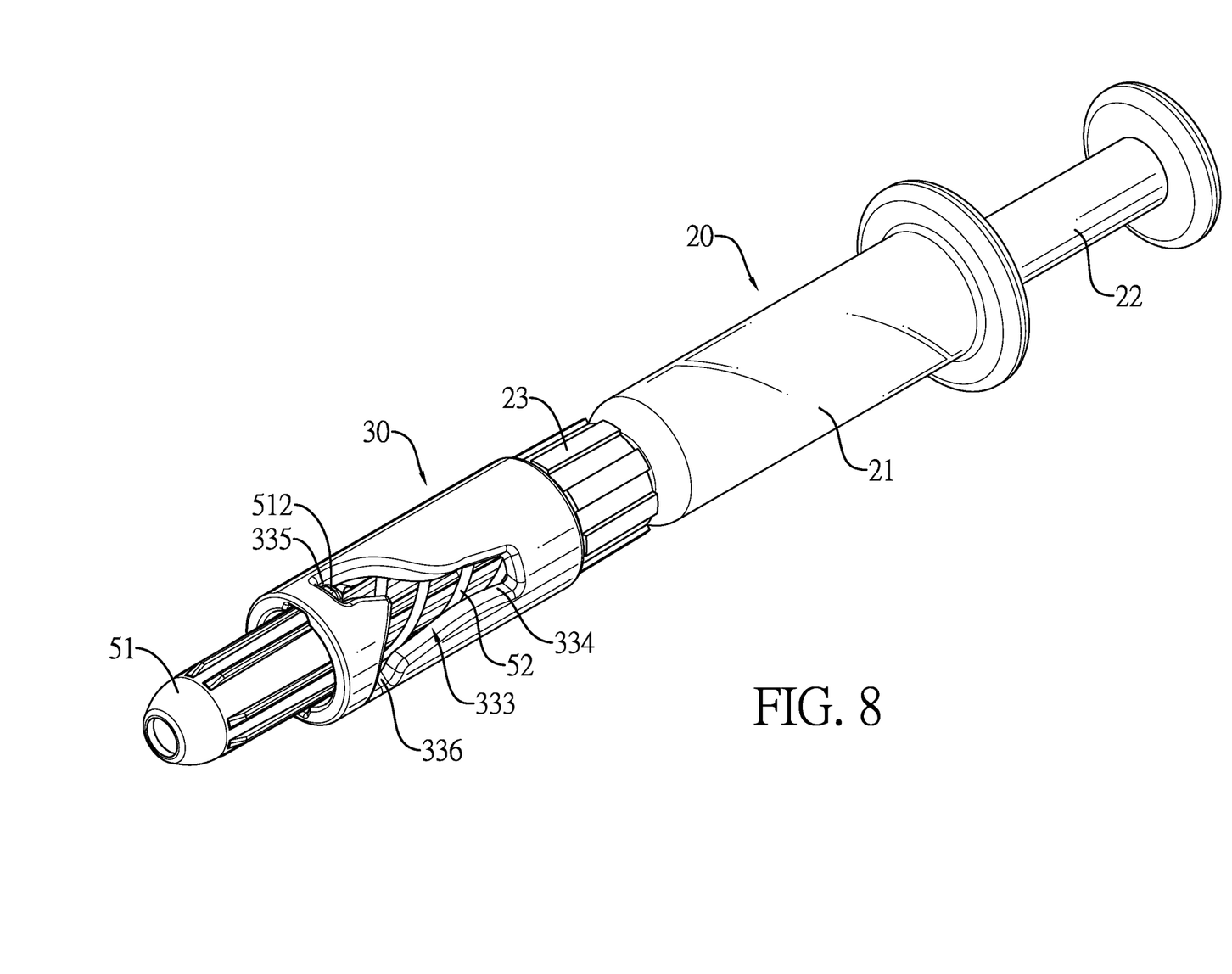
FIG. 8 is a perspective view of the safety needle in FIG. 7 with the outer cap being removed.

With reference to FIGS. 7 and 8, before the injection process, the outer cap 53 around the needle cap 51 is twisted, and the outer cap 53 is detached from the needle cap 51. Consequently, the front end of the needle cap 51 of the safety needle 10 connected with the syringe 20 extends toward a patient who is given an injection. During this process, the puncture needle 40 is kept enclosed inside the needle cap 51 to ensure safety of use.

Figure 9:
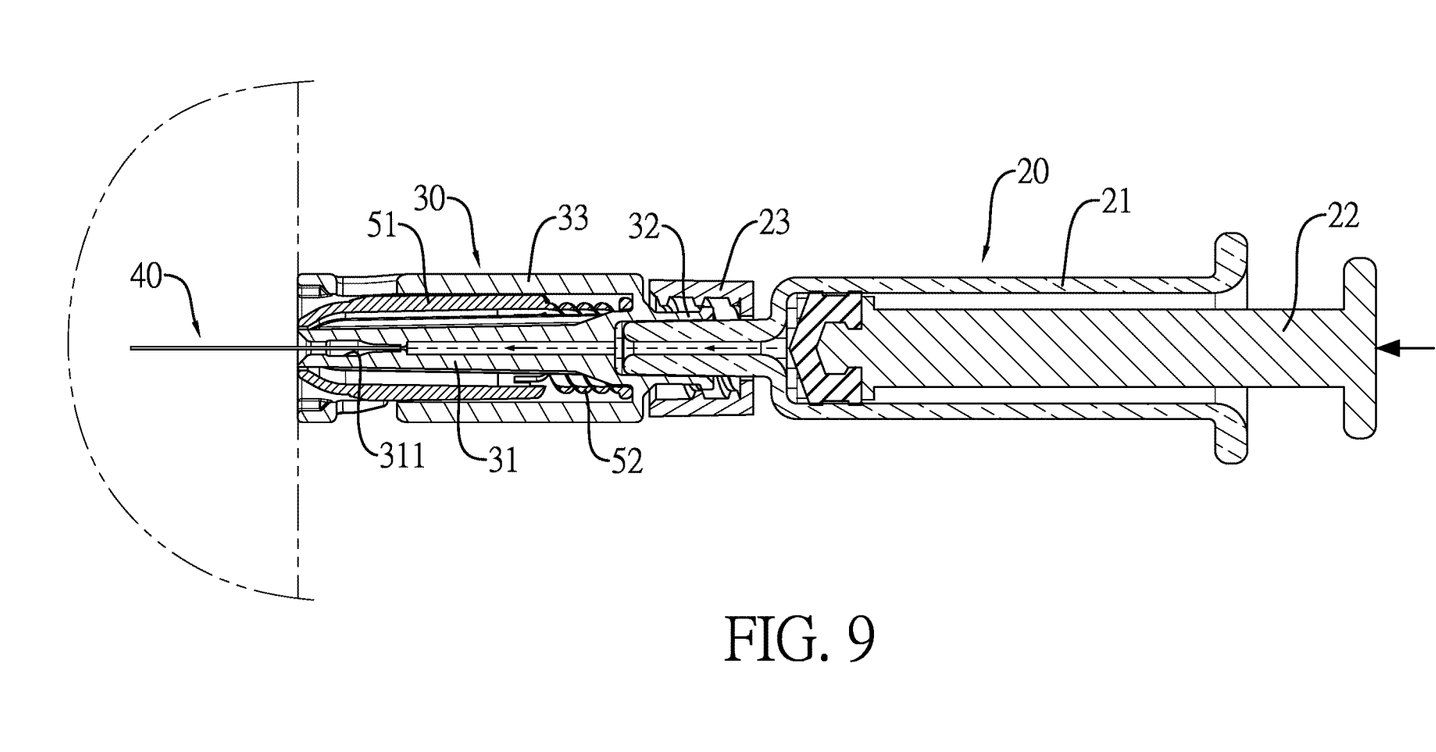
FIG. 9 is an operational cross sectional side view of the safety needle in FIG. 8, showing that the puncture needle is punctured into a human body and the plunger is pushed for injection.
Figure 10:
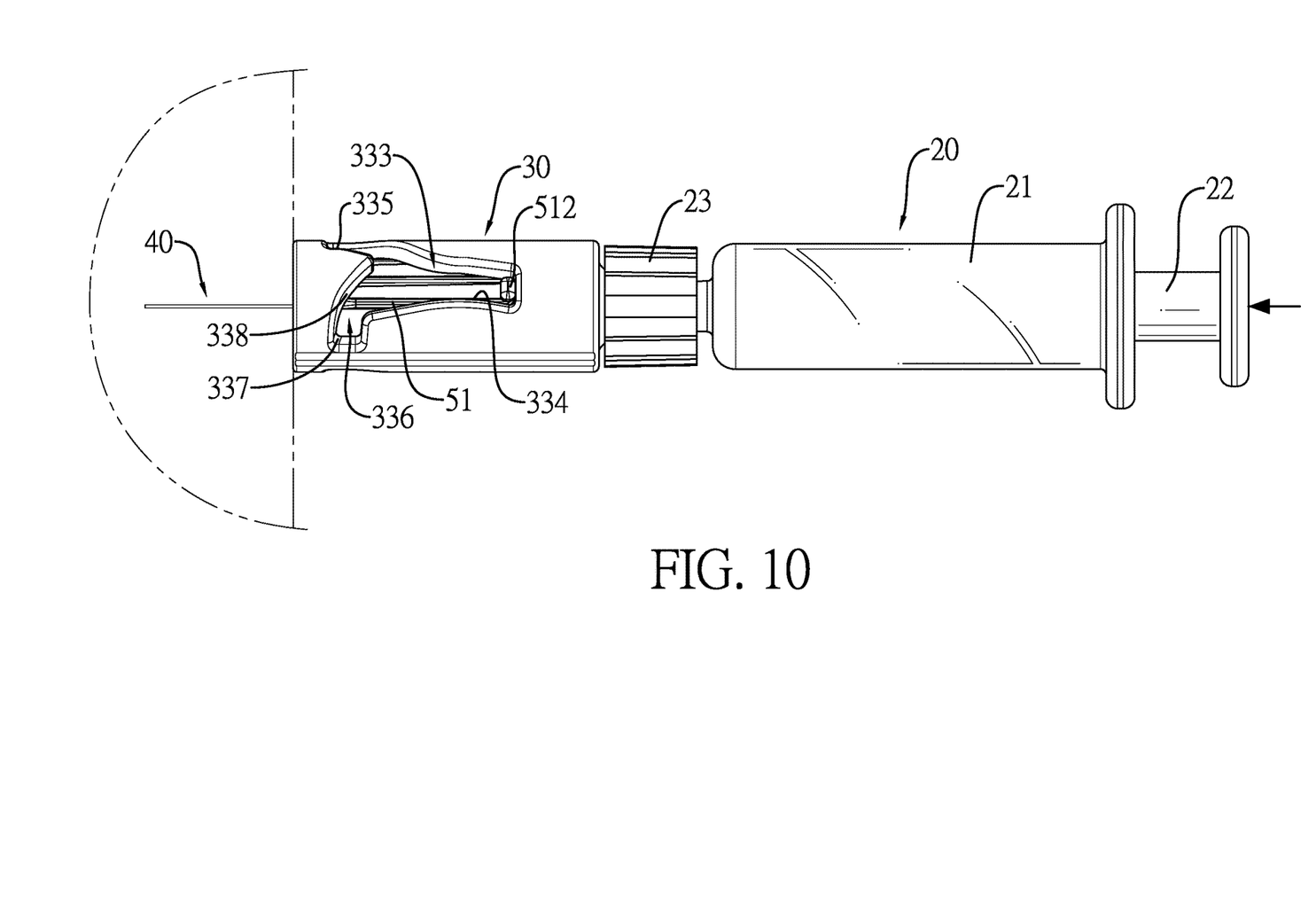
FIG. 10 is an operational side view of the safety needle in FIG. 8, showing that the puncture needle is punctured into a human body and the plunger is pushed for injection.

With reference to FIGS. 9 and 10, when the front end of the needle cap 51 abuts the skin of the patient, the syringe 20 is compressed and the needle cap 51 is pushed into the housing 33 of the needle base 30 by the compression force and the resilient member 52 is compressed. The puncture needle 40 extends out of the needle cap 51 and is punctured into the patient. During this process, the needle cap 51 is moved from the guiding section 335 toward the straight section 334 by the guiding blocks 512 moving along the positioning recesses 333 in the housing 33. The resilient member 52 is compressed by the needle cap 51. A plunger 22 of the syringe 20 is kept pushed, and the medication in the syringe 20 is injected into the patient via the needle connection segment 31 of the needle base 30 and the puncture needle 40.

Figure 11:
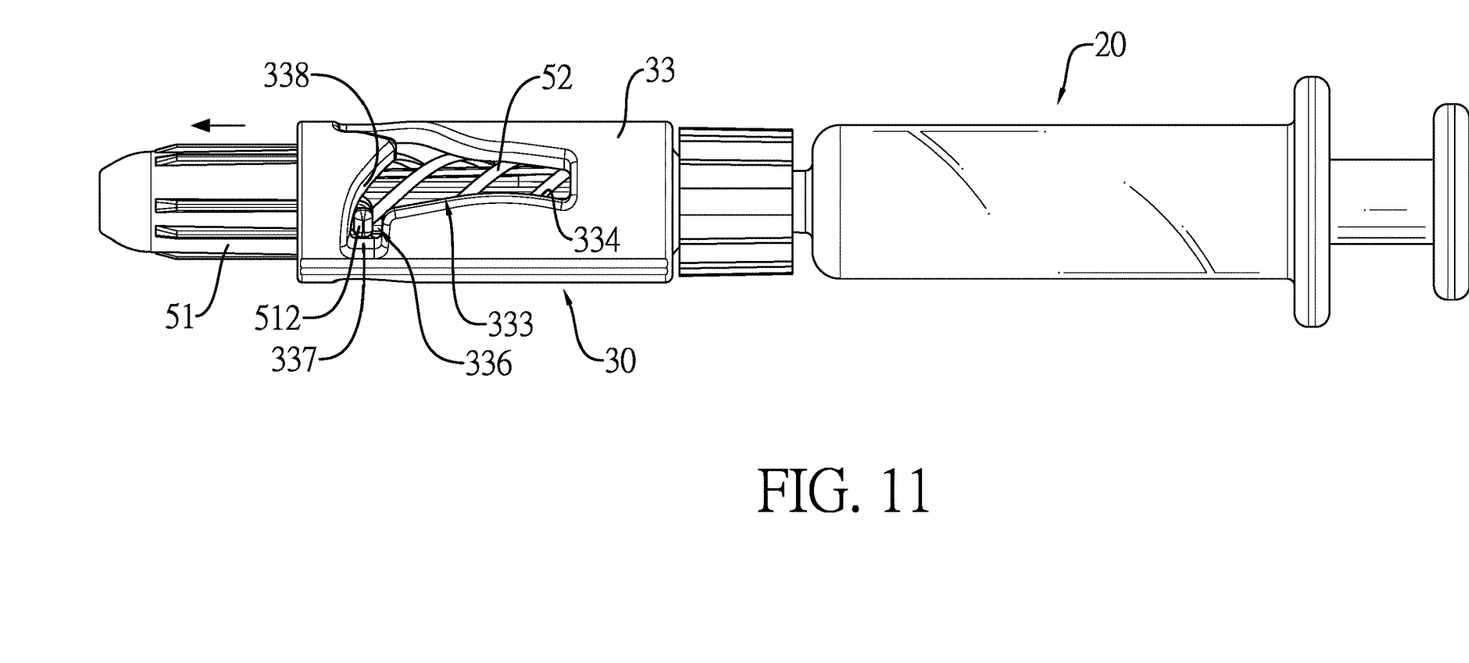
FIG. 11 is an operational side view of the safety needle in FIGS. 9 and 10, showing that the puncture needle is removed from a human body and the needle cap is pushed to extend out of the housing by a resilient member.
Figure 12:
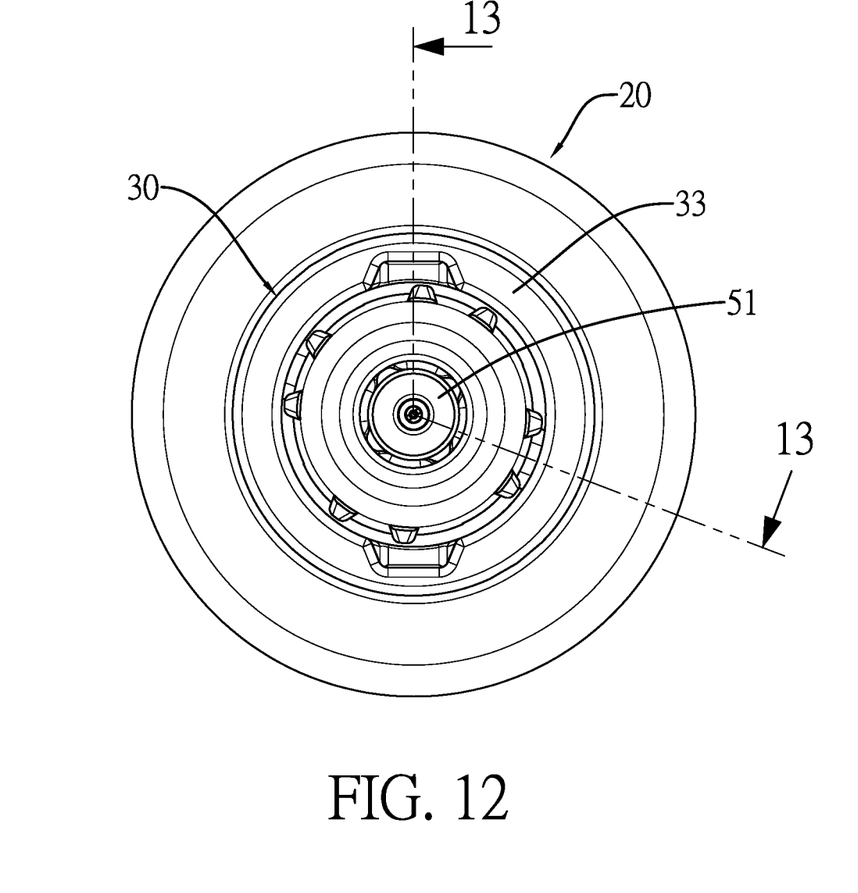
FIG. 12 is a front view of the safety needle in FIG. 11.
Figure 13:
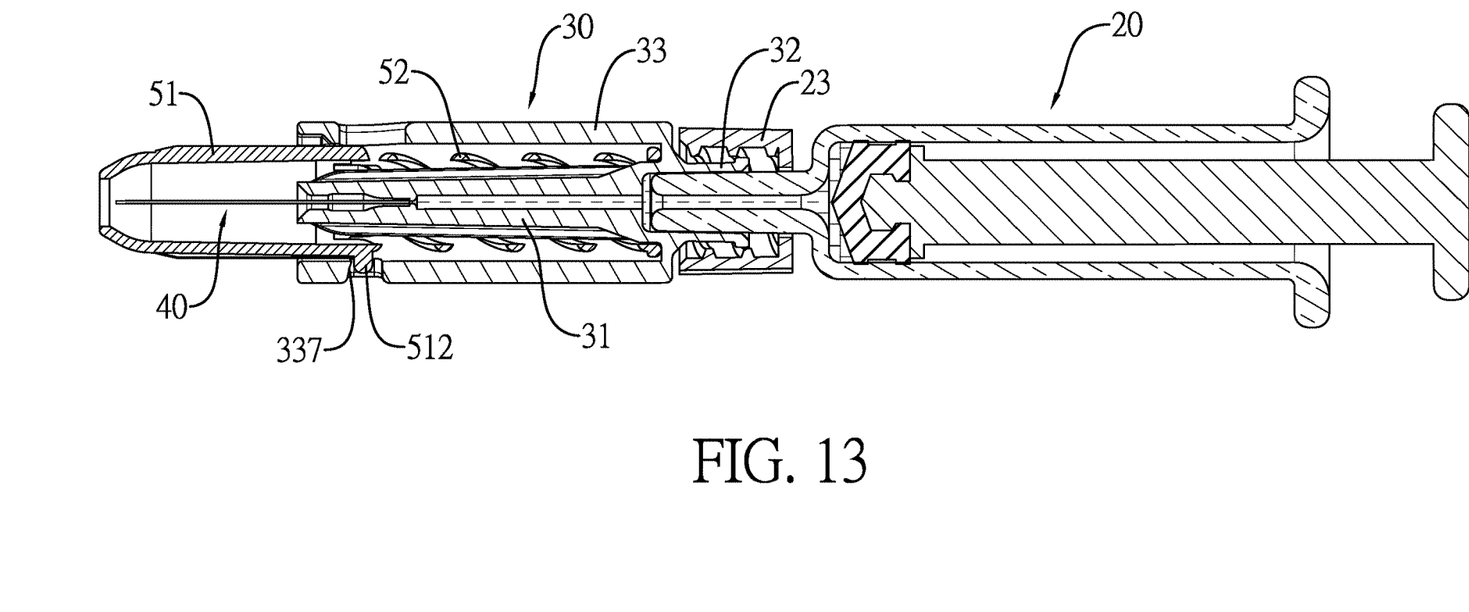
FIG. 13 is a cross sectional side view of the safety needle along the line A-A in FIG. 12.

With reference to FIGS. 11 to 13, after the medication is injected into the patient, the syringe 20 is pulled backward to move the puncture needle 40 out of the patient. At this time, the needle cap 51 is pushed to extend out of the front end of the housing 33 by the resilient member 52, and the puncture needle 40 is enclosed inside the needle cap 51. When the needle cap 51 is pushed to move forward by the resilient member 52, the guiding blocks 512 on the rear end of the needle cap 51 will move from the straight sections 334 of the positioning recesses 333, will move into the locking sections 336 by the guiding effect provided by the inclined surfaces 338, and is engaged with the locking recesses 337. The locked needle cap 51 cannot be pushed into the housing 33 of the needle base 30, such that the puncture needle 40 can be kept enclosed inside the needle cap 51. Accordingly, the safety needle 10 cannot be reused and can be easily distinguished as a used needle.

Even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A safety needle comprising:
   a needle base comprising
      a needle connection segment having a needle hole;
      a barrel connection segment formed on a rear end of the needle connection segment; and
      a housing formed around the needle connection segment to define an annular space between the needle connection segment and the housing and having
         an opening defined in a front end of the housing;
         an abutting segment formed on a rear end of the housing and connected with the rear end of the needle connection segment; and
         at least one positioning recess formed in an outer surface of the housing, and each one of the at least one positioning recess comprising
            a straight section extending along a longitudinal direction of the housing;
            a guiding section formed in the front end of the housing and having a front end and a rear end connected with a front end of the straight section; and
            a locking section formed in the front end of the housing and having a rear end connected with the front end of the straight section and being in front of the rear end of the guiding section, a locking recess defined in an end of the locking section away from the straight section, and an inclined surface formed on a front end of the locking section and extending from the front end of the straight section toward the locking recess, wherein the guiding section extends toward a direction opposite the inclined surface of the locking section;
   a puncture needle inserted into the needle hole in the needle connection segment, extending out of the front end of the housing of the needle base, and having an axial hole defined axially through the puncture needle and communicating with the needle hole in the needle connection segment; and
   a safety cap combined with a front end of the needle base and comprising
      a needle cap having a through hole defined axially through the needle cap, at least one guiding block formed on a rear end of the needle cap, and a front end;
      a resilient member extending into the annular space in the needle base, mounted around the needle connection segment, and having a front end connected with the rear end of the needle cap and a rear end connected with the abutting segment of the housing; and
      an outer cap formed around and connected integrally and detachably with the needle cap, and having
         a front end;
         a rear end selectively abutting the front end of the housing of the needle base; and
         multiple connection portions formed on the rear end of the outer cap and formed on an outer surface of the needle cap, and each connection portion having a thickness gradually decreasing toward the needle cap, wherein
   the front end of the needle cap is located inside the outer cap;
   the rear end of the needle cap extends out of the rear end of the outer cap, is held inside the housing, and is mounted around the needle connection segment;
   a gap is defined between the rear end of the outer cap and the at least one guiding block on the needle cap;
   the at least one guiding block is held respectively in the at least one positioning recess; and
   the puncture needle is held inside the needle cap and the outer cap;
   wherein before the outer cap is detached from the needle cap, the rear end of the outer cap abuts against the front end of the housing of the needle base, and the at least one guiding block of the needle cap is located at the front end of the guiding section of the at least one positioning recess;
   after the outer cap is detached from the needle cap, the needle cap is pushed into the housing of the needle base, and the at least one guiding block of the needle cap is moved along the at least one positioning recess in the housing of the needle base from the guiding section toward the straight section of the at least one positioning recess;
   when the needle cap is pushed to move out from the housing of the needle base by the resilient member, the at least one guiding block of the needle cap is moved from the straight section into the locking section by the inclined surface of the at least one positioning recess, and is engaged with the locking recess of the locking section of the at least one positioning recess.

2. The safety needle as claimed in claim 1, wherein
   the housing has two positioning recesses diametrically opposite each other; and
   the needle cap has two guiding blocks diametrically opposite each other and mounted respectively in the positioning recesses.

3. The safety needle as claimed in claim 1, wherein the barrel connection segment of the needle base comprises a sleeve and two screwing blocks formed on a rear end of the sleeve and diametrically opposite each other.

4. The safety needle as claimed in claim 2, wherein the barrel connection segment of the needle base comprises a sleeve and two screwing blocks formed on a rear end of the sleeve and diametrically opposite each other.

5. The safety needle as claimed in claim 1, wherein the resilient member is formed integrally on the rear end of the needle cap and comprises one spiral resilient strip.

6. The safety needle as claimed in claim 1, wherein the resilient member is formed integrally on the rear end of the needle cap and comprises multiple spiral resilient strips.

7. The safety needle as claimed in claim 2, wherein the resilient member is formed integrally on the rear end of the needle cap and comprises one spiral resilient strip.

8. The safety needle as claimed in claim 2, wherein the resilient member is formed integrally on the rear end of the needle cap and comprises multiple spiral resilient strips.

9. The safety needle as claimed in claim 3, wherein the resilient member is formed integrally on the rear end of the needle cap and comprises one spiral resilient strip.

10. The safety needle as claimed in claim 3, wherein the resilient member is formed integrally on the rear end of the needle cap and comprises multiple spiral resilient strips.

11. The safety needle as claimed in claim 4, wherein the resilient member is formed integrally on the rear end of the needle cap and comprises one spiral resilient strip.

12. The safety needle as claimed in claim 4, wherein the resilient member is formed integrally on the rear end of the needle cap and comprises multiple spiral resilient strips.

* * * * *